US012290551B2

(12) United States Patent
Moraitis (10) Patent No.: US 12,290,551 B2
(45) Date of Patent: May 6, 2025

(54) METHODS FOR IMAGING AND TREATMENT OF SOMATOSTATIN-RECEPTOR POSITIVE TUMORS

(71) Applicant: Corcept Therapeutics Incorporated, Menlo Park, CA (US)

(72) Inventor: Andreas G. Moraitis, Sunny Isles Beach, FL (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 833 days.

(21) Appl. No.: 17/418,120

(22) PCT Filed: Dec. 19, 2019

(86) PCT No.: PCT/US2019/067341
§ 371 (c)(1),
(2) Date: Jun. 24, 2021

(87) PCT Pub. No.: WO2020/132171
PCT Pub. Date: Jun. 25, 2020

(65) Prior Publication Data
US 2022/0062386 A1  Mar. 3, 2022

Related U.S. Application Data

(60) Provisional application No. 62/783,015, filed on Dec. 20, 2018.

(51) Int. Cl.
*A61K 38/31* (2006.01)
*A61K 31/4745* (2006.01)
(Continued)

(52) U.S. Cl.
CPC .......... *A61K 38/31* (2013.01); *A61K 31/4745* (2013.01); *A61K 51/083* (2013.01); *A61P 35/00* (2018.01)

(58) Field of Classification Search
None
See application file for complete search history.

(56) References Cited

U.S. PATENT DOCUMENTS

| 8,859,774 B2 | 10/2014 | Hunt et al. |
| 2017/0273972 A1* | 9/2017 | Hunt .................... C07D 471/04 |

(Continued)

FOREIGN PATENT DOCUMENTS

| CN | 108137690 A | 6/2018 |
| JP | 7444889 B2 | 2/2024 |

(Continued)

OTHER PUBLICATIONS

"A Study of the Efficacy and Safety of Relacorilant in Patients With Endogenous Cushing Syndrome", US National Library of Medicines, Available Online at:- https://clinicaltrials.gov/ct2/show/NC 703697109, Oct. 5, 2018, 8 pages.

(Continued)

*Primary Examiner* — Jake M Vu
(74) *Attorney, Agent, or Firm* — Kilpatrick Townsend & Stockton LLP (57) ABSTRACT

Methods for treating, identifying and localizing tumors expressing somatostatin receptors (SRs), including methods of enhancing the efficacy of imaging techniques by administration of a heteroaryl-ketone fused azadecalin glucocorticoid receptor modulator (HKGRM) effective to increase SR expression in tumors. HKGRM administration for enhancing SR-based tumor imaging and treating neuroendocrine tumors. HKGRM and somatostatin or somatostatin analog combination therapy for treating and enhancing SR-based tumor imaging.

8 Claims, 2 Drawing Sheets

(51) Int. Cl.
    *A61K 51/08*     (2006.01)
    *A61P 35/00*     (2006.01)

(56) References Cited

U.S. PATENT DOCUMENTS

2018/0125856 A1    5/2018    Moraitis et al.
2018/0256604 A1    9/2018    Moraitis

FOREIGN PATENT DOCUMENTS

WO    WO-2016140867 A1 *  9/2016  ........... A61K 31/437
WO       2020097513 A1    5/2020

OTHER PUBLICATIONS

European Patent Application No. 19899701.7, "Partial Supplementary European Search Report", Aug. 3, 2022, 14 pages.
Singapore Patent Application No. 11202105746T, "Written Opinion", Aug. 10, 2022, 8 pages.
PCT/US2019/067341, "International Search Report and Written Opinion", Feb. 24, 2020, 13 pages.
Yoshioka et al., "A Case of the Watery Diarrhea-Hypokalemia-Achlorhydria Syndrome: Successful Preoperative Treatment of Watery Diarrhea With a Somatostatin Analogue", Japanese Journal of Clinical Oncology, vol. 19, Issue 3, 1989, pp. 294-298, Abstract only.
Chinese Patent Application No. 201980084219.5, "Office Action", Jun. 7, 2024, 11 pages.
Israeli Patent Application No. 284237, "Notice of Allowance", Jul. 30, 2024, 4 pages.

* cited by examiner

METHODS FOR IMAGING AND TREATMENT OF SOMATOSTATIN-RECEPTOR POSITIVE TUMORS

CROSS-REFERENCE TO RELATED APPLICATIONS

This application claims the benefit of, and priority to, U.S. Patent Application 62/783,015 filed Dec. 20, 2018, the entire contents of which application is hereby incorporated by references in its entirety.

BACKGROUND

Detection, identification, localization, and treatment of tumors and metastases is critical in treating cancer, and in treating disorders resulting from such tumors or metastases. Cushing's syndrome is typically due to excess adrenocorticotropic hormone (ACTH) or cortisol secretion by a tumor, such as, e.g., a neuroendocrine tumor. Tumors that express the somatostatin receptor (SR), such as SR subtypes sst2 sst3 or sst5, can be visualized in vivo by injection of radiolabeled somatostatin analogs (SSAs). Such imaging (which may be termed "scintigraphy") is useful for imaging and localization of such tumors, may aid in identification, and may aid in staging of the disease. (e.g., by other imaging techniques and technologies). Such imaging may allow detection of tumors that otherwise would not have been detected, and which would have otherwise remained invisible or unrecognized using conventional imaging techniques.

Cortisol is a steroid hormone produced by the adrenal glands which acts by binding to glucocorticoid receptors (GRs) in target cells. Cortisol is used in the body to respond to physical and emotional stress, and maintain adequate energy supply and blood sugar levels. Cortisol production is highly regulated by the hypothalamic-pituitary-adrenal axis (HPA) through a complex set of direct influences and negative feedback interactions. In healthy individuals, insufficient cortisol in the bloodstream triggers the hypothalamus to release corticotropin-releasing hormone (CRH) which signals to the pituitary gland to release adrenocorticotropic hormone (ACTH), which in turn stimulates the adrenal glands to produce more cortisol. Excessive cortisol inhibits the hypothalamus from producing CRH, thus inhibiting the pituitary gland from releasing ACTH, which in turn suppresses cortisol production. Pathological conditions associated with the HPA can affect the diurnal rhythm of the cortisol and ACTH production and cause serious health problems. Excess production of CRH, ACTH, or cortisol, e.g., by a tumor, may thus cause serious health problems in addition to those caused by the mere presence of the tumor.

The biological effects of cortisol, including those caused by hypercortisolemia, can be modulated at the GR level using receptor modulators (GRMs), which can act as GR agonists (e.g., mimicking cortisol), partial agonists and antagonists (e.g., inhibiting the effects of cortisol). Several different classes of agents are able to inhibit the physiologic effects of GR-agonist binding. These antagonists include compositions which, by binding to GR, reduce the ability of an agonist to effectively bind to and/or activate the GR. One such known GRM is the GR antagonist (GRA) mifepristone, has been found to be an effective anti-glucocorticoid agent in humans (Bertagna (1984) J. Clin. Endocrinol. Metab. 59:25). Mifepristone binds to the GR with high affinity, with a dissociation constant ($K_d$) of $10^{-9}$ M (Cadepond (1997) Annu. Rev. Med. 48:129).

Hypercortisolism, often referred to as Cushing's syndrome, is caused by excessive activity of the stress hormone cortisol. Symptoms vary, but most people experience one or more of the following manifestations: high blood sugar (hyperglycemia), diabetes, high blood pressure, upper-body obesity, rounded face, increased fat around the neck, thinning arms and legs, easy bruising, facial plethora, acne, red purple stripes across the body, severe fatigue and weak muscles. Irritability, anxiety, cognitive disturbances and depression are also common. Cushing's syndrome can affect every organ system in the body and can be lethal if not treated effectively.

Cushing's syndrome can be classified as exogenous Cushing's syndrome, which is caused by excess use of glucocorticoid drugs (which are sometimes also termed corticosteroids), such as prednisone, dexamethasone, and hydrocortisone, and endogenous Cushing's syndrome, which is caused by deregulatory abnormalities in the HPA axis. Endogenous Cushing's syndrome consists of the ACTH-independent Cushing's syndrome, characterized by an overproduction of cortisol in the absence of elevation of ACTH secretion; and the ACTH-dependent Cushing's syndrome, characterized by excessive ACTH secretion.

ACTH-dependent Cushing's syndrome includes roughly 80% of patients having endogenous Cushing's syndrome and consists of two major forms: Cushing Disease and ectopic ACTH syndrome. The former is caused by a pituitary tumor and the latter is caused by a tumor outside the pituitary, such as, e.g., an adrenal tumor. Correct differential diagnosis between ACTH-Dependent Cushing's syndrome on the one hand, and ectopic ACTH syndrome (e.g., adrenal Cushing's syndrome) or exogenous Cushing's syndrome on the other hand, is important for endocrinologists to recommend transsphenoidal surgery, reduction or cessation of glucocorticoid administration (for exogenous Cushing's syndrome), or appropriate imaging to localize and identify the source of the ectopic ACTH secretion.

Cushing's syndrome patients may be treated by GRMs, such as mifepristone, to reduce or block the effects of excess cortisol (see, e.g., U.S. Pat. Nos. 9,943,526; 9,956,216, both of which patents are hereby incorporated by reference in their entireties). In addition, heteroaryl-ketone fused azadecalin compounds may bind to glucocorticoid receptors (GRs), may act as GRMs, and may thereby have therapeutic activity. Such compounds and their activities are disclosed, for example, in U.S. Pat. Nos. 8,859,774; 9,273,047; 9,707,223; 9,943,505; 9,956,216; and others. Pharmaceutical formulations containing heteroaryl-ketone fused azadecalin compounds may be used for administration of those compounds to humans or animals for therapeutic purposes.

Cushing's syndrome patients may be treated surgically to remove, as much as possible, the source of the excess cortisol, and by other means. However, it may be critical to identify, or to localize, the source of excess cortisol. In addition, since mifepristone blocks cortisol activation of GR, cortisol levels often increase in Cushing's syndrome patients treated with mifepristone, possibly leading to hypokalemia due to cortisol action on mineralocorticoid receptors. Hypokalemia may be a serious condition requiring medical treatment to correct.

Accordingly, methods for detecting, locating, identifying, and treating tumors are needed. Methods for detecting, locating, identifying, and treating tumors which may cause Cushing's syndrome in patients who suffer from Cushing's syndrome are needed. In addition, improved imaging methods for identifying those Cushing's syndrome patients who suffer from ACTH-Dependent Cushing's syndrome who are in need of transsphenoidal surgery, or for whom transsphenoidal was incompletely successful or was unsuccessful; and for identifying those Cushing's syndrome patients who suffer from adrenal Cushing's syndrome or who suffer from ectopic Cushing's syndrome due to other tumors apart from adrenal tumors, are needed.

SUMMARY

Applicant has surprisingly discovered that the heteroaryl-ketone fused azadecalin glucocorticoid receptor modulator (GRM) termed "relacorilant" is an effective glucocorticoid receptor antagonist (GRA) that can inhibit glucocorticoid receptor (GR) activation without raising cortisol levels, and thus without increasing the risk of hypokalemia in patients. Administration of heteroaryl-ketone fused azadecalin GRMs effective to block GR activation also stimulates somatostatin receptor (SR) expression. Provided herein are methods for treating, identifying and localizing tumors expressing SR, including methods of enhancing the efficacy of imaging techniques by increasing SR expression in tumors. In preferred methods, the heteroaryl-ketone fused azadecalin GRM is relacorilant. In embodiments, the methods include selecting patients who may derive benefit from the treatment methods disclosed herein. Patients who may derive benefit from the treatment methods disclosed herein include those suspected of hosting a tumor, where the suspected tumor expresses low levels of somatostatin receptors, or where the suspected tumor is not visible, or is poorly visible, with imaging techniques such as techniques used to image somatostatin receptors, or where increasing said somatostatin receptor expression in the tumor would improve imaging, identification, or localization of the tumor, and combinations thereof.

Applicant discloses herein methods of treating a tumor in a patient hosting a tumor without increasing cortisol levels or risk of hypokalemia in the patient, the tumor having a baseline level of somatostatin receptor expression, the method comprising: a) Administering to the patient at least one dose of a heteroaryl-ketone fused azadecalin GRM, effective stimulate the expression of SRs in said tumor; and b) administering to the patient at least one dose of somatostatin or a somatostatin analog; whereby the tumor is treated without increasing cortisol levels or risk of hypokalemia in the patient. In embodiments, administration of a heteroaryl-ketone fused azadecalin GRM compound is effective to enhance SR expression and improve treatment, identification, and localization of a tumor while not leading to significant increases in cortisol, and while not increasing the risk of, or causing, hypokalemia. The tumors may be, e.g., neuroendocrine tumors. In embodiments, the tumor is a neuroendocrine tumor, and the methods include methods of treating a neuroendocrine tumor in a patient hosting a neuroendocrine tumor without increasing cortisol levels or risk of hypokalemia in the patient, the tumor having a baseline level of somatostatin receptor expression, the method comprising: a) Administering to the patient at least one dose of a heteroaryl-ketone fused azadecalin GRM, effective stimulate the expression of somatostatin receptors (SRs) in said neuroendocrine tumor; and b) administering to the patient at least one dose of somatostatin or a somatostatin analog; whereby the neuroendocrine tumor is treated, without leading to significant increases in cortisol, and while not increasing the risk of, or causing, hypokalemia. These methods are useful for treating, locating and identifying tumors suspected of causing Cushing's syndrome in patients.

Poor SR expression in a tumor may be determined by low-level (faint) or non-existent images of the tumor with SR imaging. In embodiments, a patient suffering from Cushing's syndrome having a tumor that expresses no, or only small amounts of, somatostatin receptor (SR) is selected for the methods disclosed herein in order to enhance imaging of a tumor by increasing SR expression in the tumor. In embodiments, these methods are useful for enhancing imaging techniques so as to improve imaging, locating, or identifying tumors in a patient, such as a Cushing's syndrome patient. In embodiments, these methods are useful in some cases, so as to make it possible to obtain usable images of a tumor, or to determine the location of a tumor, or to identify a tumor, where i) such images, location, or identification of a tumor would otherwise would not have been possible, or ii) where obtaining such images, location, or identification of a tumor would otherwise would not have been possible without increasing cortisol levels or risk of hypokalemia in the patient, or both i) and ii). Heteroaryl-ketone fused azadecalin GRMs bind to glucocorticoid receptors (GRs) and may increase somatostatin receptor expression, particularly may increase expression of somatostatin receptor type 2 (sst2) in tumors. SR, including sst2, bind octreotide and other SR ligands. Treatment of patients hosting a tumor with a heteroaryl-ketone fused azadecalin GRM may be, by itself, effective to treat such a tumor. Treatment of patients hosting a tumor with a heteroaryl-ketone fused azadecalin GRM is shown to be effective to enhance SR-based imaging of such a tumor, improving diagnosis and localization of the tumor. Such enhanced imaging allows better determination of the further course of tumor treatment, whether surgery, radiation, chemotherapy, or combinations thereof, than was provided by prior methods. Improved localization of the tumor by such enhanced imaging allows for improved surgery, radiation, or both.

Enhancement of SR expression by GRM administration also enhances treatment of tumors, such as neuroendocrine tumors, in combination with somatostatin analogs or with peptide receptor radionuclide therapy. In embodiments, the treatment of neuroendocrine tumors comprises administration of a heteroaryl-ketone fused azadecalin GRM and a somatostatin receptor agonist, such as, e.g., somatostatin or a somatostatin analog (SSA). In embodiments, the somatostatin or SSA is a radiolabeled somatostatin or SSA.

In some embodiments, the method comprises administering a somatostatin analog (SSA). In some cases, the SSA is selected from the group consisting of octreotide, octreotate, pasireotide, lanreotide, pentetreotide, and derivatives thereof. In some cases, the SSA is labeled with a radionuclide, such as, e.g., $^{111}$Indium, $^{90}$Yterbium, $^{177}$Lutetium, $^{213}$Bismuth, or other radionuclides. Examples of radiolabeled SSAs include, for example, $^{123}$I-Tyr$^3$-octreotide, $^{111}$In-DTPA-D-Phe$^1$-octreotide, [$^{111}$In-DTPA$^0$]octreotide, [$^{90}$Y-DOTA, Tyr$^3$]octreotide, $^{111}$In-octreotide, $^{111}$In-pentetreotide, and [$^{177}$Lu-DOTA, Tyr$^3$]octreotate. Such radiolabeled SSAs are used, for example, in peptide receptor radionuclide imaging for observing, localizing, or identifying tumors in patients. In embodiments, such tumors may be, e.g., neuroendocrine tumors, and may be inoperable and/or metastatic neuroendocrine tumors. Such radiolabeled SSAs are used, for example, in peptide receptor radionuclide therapy (PRRT) for patients with inoperable and/or metastatic tumors, such as inoperable and/or metastatic neuroendocrine tumors. Administration of a SSA in combination with heteroaryl-ketone fused azadecalin GRM administration, or following heteroaryl-ketone fused azadecalin GRM administration, or both, enhances SSA imaging and PRRT as compared to such imaging in the absence of heteroaryl-ketone fused azadecalin GRM administration.

In some cases, the SSA is administered in a sustained release formulation. In some cases, the SSA is administered as octreotide LAR (such as, e.g., Sandostatin® LAR depot, a composition of octreotide acetate formulated for injection, as a suspension).

Enhancement of SR expression by a heteroaryl-ketone fused azadecalin GRM compound has advantages as compared to administration of other GRM compounds, in that administration of a heteroaryl-ketone fused azadecalin GRM compound does not lead to significant increases in cortisol. For example, as disclosed herein, administration of the heteroaryl-ketone fused azadecalin GRM compound "relacorilant" did not lead to significant increases in cortisol in Cushing's syndrome patients to whom it was administered; this is important since Cushing's syndrome patients already suffer from excess cortisol, leading to risk of hypokalemia, a serious condition requiring immediate medical attention. Relacorilant administration thus did not lead to further increased risk of hypokalemia; however, such increased risk of hypokalemia may follow administration of other GRMs; for example, hypokalemia was observed in 44% of subjects during treatment with mifepristone (Korlym®) (Korlym FDA Label, section 5.2) administration also enhances treatment of neuroendocrine tumors in combination with somatostatin analogs or with peptide receptor radionuclide imaging or peptide receptor radionuclide therapy. Excess cortisol may also lead to endometrial hypertrophy, vaginal bleeding, or other complications in female patients, and the risk, or severity, of such adverse events may be increased by mifepristone administration in female Cushing's syndrome patients. However, the heteroaryl-ketone fused azadecalin GRM compound relacorilant also binds to GR and modulates the effects of cortisol, but does not significantly increase cortisol levels, and thus would not significantly increase adverse events associated with further increases in cortisol levels. Thus, heteroaryl-ketone fused azadecalin GRM compounds, such as relacorilant, may be administered and used to image tumors, enhance tumor images, localize tumors, and treat tumors yet would not be expected to significantly increase cortisol levels, and thus may be administered and used for imaging, diagnosis, and therapy where modulation of GR, modulation of somatostatin receptor expression, or both, is involved, without significantly increasing adverse events associated with further increases in cortisol levels.

Administration of a heteroaryl-ketone fused azadecalin GRM compound, such as relacorilant, is thus useful to image, to localize, to identify, and to treat tumors, such as neuroendocrine tumors while not leading to significant increases in cortisol, and while not increasing the risk of, or causing, hypokalemia. Administration of a heteroaryl-ketone fused azadecalin GRM, such as relacorilant, provides the diagnostic and therapeutic benefits of GRM administration without such increased risks. Accordingly, the present methods provide advantages as compared to prior methods.

The methods disclosed herein provide advantages of treating Cushing's syndrome in a patient suffering from Cushing's syndrome, while at the same time providing further diagnostic information useful for imaging, localization, or identification of a tumor associated with, or causing, Cushing's syndrome while not leading to significant increases in cortisol, and while not increasing the risk of, or causing, hypokalemia. Such a tumor associated with, or causing, Cushing's syndrome may be a pituitary tumor, an adrenal tumor, may be a tumor located elsewhere in the body of the patient, and may be one of more than one tumor associated with, or causing, Cushing's syndrome. In embodiments, the tumor may be a neuroendocrine tumor.

In embodiments, identifying information, localization information, and diagnostic information obtained by the methods disclosed herein may be useful to aid in providing the patient with appropriate treatment; may avoid unnecessary delay in treating a serious medical condition; may aid in determining whether or not further treatment is needed; and may aid in determining what type of further treatment may be needed (e.g., typically transsphenoidal surgery for patients identified as having ACTH-dependent Cushing's syndrome; adrenal surgery for an adrenal tumor for patients identified as having adrenal Cushing's syndrome; or other surgery for a tumor identified or localized as other than a pituitary or adrenal tumor). All these advantages may be obtained while not leading to significant increases in cortisol, and while not increasing the risk of, or causing, hypokalemia, providing advantages over prior treatments and imaging methods.

Other objects, features, and advantages of the methods disclosed herein will be apparent to one of skill in the art from the following detailed description and figures.

DETAILED DESCRIPTION

I. Introduction

Applicant provides novel methods for identifying and localizing tumors expressing somatostatin receptors, including methods of enhancing the efficacy of imaging techniques by increasing somatostatin receptor (SR) expression in tumors while not leading to significant increases in cortisol, and while not increasing the risk of, or causing, hypokalemia. Heteroaryl-ketone fused azadecalin glucocorticoid receptor modulators (GRMs) bind to glucocorticoid receptors (GRs) and may increase somatostatin receptor expression, particularly may increase expression of somatostatin receptor type 2 (sst2) in tumors. SRs, including sst2, bind octreotide and other SR ligands. Treatment of patients hosting a tumor with a heteroaryl-ketone fused azadecalin GRM may be, by itself, effective to treat such a tumor. Treatment of patients hosting a tumor with a heteroaryl-ketone fused azadecalin GRM is shown to be effective to enhance SR-based imaging of such a tumor, improving diagnosis and localization of the tumor. Such enhanced imaging allows better determination of the further course of tumor treatment, whether surgery, radiation, chemotherapy, or combinations thereof, than was provided by prior methods, while further not leading to significant increases in cortisol, and while not increasing the risk of, or causing, hypokalemia. Improved localization of the tumor by such heteroaryl-ketone fused azadecalin GRM-enhanced imaging allows for improved treatment outcomes for surgery, radiation, or both as compared to such treatment outcomes in the absence of such enhanced imaging. Enhancement of SR expression by such GRM administration also enhances treatment of tumors, such as neuroendocrine tumors by administration of heteroaryl-ketone fused azadecalin GRMs such as relacorilant, in combination with somatostatin analogs or with peptide receptor radionuclide imaging or peptide receptor radionuclide therapy while not leading to significant increases in cortisol, and while not increasing the risk of, or causing, hypokalemia.

In embodiments, a patient is selected for treatment by the methods disclosed herein due to poor SR imaging, where the patient is in need of enhancement of such imaging. Poor SR expression in a tumor may be determined by low-level (faint) or non-existent images of the tumor with SR imaging. In embodiments, a patient suffering from Cushing's syndrome having a tumor that expresses no, or only small amounts of, somatostatin receptor (SR) is selected for the methods disclosed herein in order to enhance imaging of a tumor by increasing SR expression in the tumor. In embodiments, these methods are useful for enhancing imaging techniques so as to improve imaging, locating, or identifying tumors in a patient, such as a Cushing's syndrome patient. In embodiments, these methods are useful in some cases, so as to make it possible to obtain usable images of a tumor, or to determine the location of a tumor, or to identify a tumor, where i) such images, location, or identification of a tumor would otherwise would not have been possible, or ii) where obtaining such images, location, or identification of a tumor would otherwise would not have been possible without increasing cortisol levels or risk of hypokalemia in the patient, or both i) and ii).

Heteroaryl-ketone fused azadecalin GRM compounds are disclosed, for example, in U.S. Pat. No. 8,859,774, and other patents. In embodiments, heteroaryl-ketone fused azadecalin GRM compounds suitable for use in the practice of the methods disclosed herein include relacorilant (also termed "CORT125134"), CORT122928, CORT113176, and other heteroaryl-ketone fused azadecalin GRM compounds disclosed in U.S. Pat. No. 8,859,774 and continuations thereof.

In some embodiments, the method comprises administering a somatostatin analog (SSA) in combination with a heteroaryl-ketone fused azadecalin GRM (such as, e.g., relacorilant). In some cases, the SSA is labeled with a radionuclide, such as, e.g., $^{111}$Indium, $^{90}$Yterbium, $^{177}$Lutetium, $^{213}$Bismuth, or other radionuclides. Such radiolabeled SSAs are used, for example, in peptide receptor radionuclide therapy (PRRT) for patients with inoperable and/or metastatic tumors, such as inoperable and/or metastatic neuroendocrine tumors. Examples of radiolabeled SSAs include, for example, $^{123}$I-Tyr$^3$-octreotide, $^{111}$In-DTPA-D-Phe$^1$-octreotide, [$^{111}$In-DTPA$^0$]octreotide, [$^{90}$Y-DOTA, Tyr$^3$]octreotide, $^{111}$In-octreotide, $^{111}$In-pentetreotide, and [$^{177}$Lu-DOTA, Tyr$^3$]octreotate. In some cases, the somatostatin analog is administered in a sustained release formulation. In some cases, the somatostatin analog is administered as octreotide LAR (such as, e.g., Sandostatin® LAR depot, a composition of octreotide acetate formulated for injection, as a suspension).

Applicant discloses herein formulations comprising the heteroaryl-ketone fused azadecalin GRM compounds for use with somatostatin or with somatostatin analogs. Such uses include, without limitation, for example, use of heteroaryl-ketone fused azadecalin GRM compounds with somatostatin or SSAs for identifying and localizing tumors expressing somatostatin receptors, including methods of enhancing the efficacy of imaging techniques by increasing somatostatin receptor (SR) expression in tumors. Such uses include, without limitation, for example, use of heteroaryl-ketone fused azadecalin GRM compounds with somatostatin or SSAs for treating tumors, including treating tumors expressing somatostatin receptors; in embodiments, the somatostatin or SSA is radiolabeled. Such uses include, without limitation, for example, use of heteroaryl-ketone fused azadecalin GRM compounds in combination with somatostatin or SSAs for treating tumors, where the method comprises peptide receptor radionuclide imaging or peptide receptor radionuclide therapy.

Heteroaryl-ketone fused azadecalin compounds are described in U.S. Pat. No. 8,859,774; in U.S. Pat. No. 9,273,047; in U.S. Pat. No. 9,707,223; and in U.S. Pat. No. 9,956,216, all of which patents are hereby incorporated by reference in their entireties. In embodiments, the heteroaryl-ketone fused azadecalin GRM is the compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl) pyridin-2-yl)methanone (Example 18 of U.S. Pat. No. 8,859,774), also known as "relacorilant" and as "CORT125134", which has the following structure:

In embodiments, the heteroaryl-ketone fused azadecalin GRM is the compound (R)-(1-(4-fluorophenyl)-6-((4-(trifluoromethyl)phenyl)sulfonyl)-4,4a,5,6,-7,8-hexahydro-1H-pyrazolo[3,4-g]isoquinolin-4a-yl)(thiazol-2-yl)methanone (termed "CORT122928"), which has the following structure:

In embodiments, the heteroaryl-ketone fused azadecalin GRM is the compound (R)-(1-(4-fluorophenyl)-6-((4-(trifluoromethyl)phenyl)sulfonyl)-4, 4a, 5,6,7,8-hexahydro-1-H-pyrazolo P,4-g]isoquinolin-4a-yl) (pyridin-2-yl)methanone (termed "CORT113176"), which has the following structure:

In embodiments, the formulations disclosed herein are suitable for pharmaceutical use, and have improved stability and bioavailability as compared to prior or alternative formulations. In embodiments, the formulations may include relacorilant and a pharmaceutically acceptable excipient. In embodiments, the formulations contain relacorilant and a pharmaceutically acceptable excipient and are suitable for use in pharmaceutical compositions for oral administration of relacorilant to human patients for treating a disease or disorder, or to animals for veterinary therapeutic purposes.

In embodiments, the pharmaceutical formulation is suitable for the administration of an effective amount of relacorilant, e.g., a daily dose of relacorilant of between about 1 and 100 mg/kg/day, preferably a daily dose of relacorilant of between about 1 and 20 mg/kg/day. In embodiments, the pharmaceutical formulation is suitable for the administration of an effective amount of relacorilant, e.g., in a unit dose formulation containing between about 1 and about 500 milligrams (mg) of relacorilant. In embodiments, such a unit dose formulation of relacorilant contains 10 milligrams (mg), or 15 mg, or 20 mg, or 25 mg, or 50 mg, or 100 mg, or 150 mg, or 200 mg, or 250 mg, or 300 mg, or 350 mg, or 400 mg, or 450 mg, or 500 mg, or 600 mg, or 700 mg, or 750 mg, of relacorilant.

In embodiments, the heteroaryl-ketone fused azadecalin GRM compound, such as, e.g., relacorilant, is administered orally. In embodiments, the heteroaryl-ketone fused azadecalin GRM compound, such as, e.g., relacorilant, is administered on a daily basis; for example, in embodiments, the heteroaryl-ketone fused azadecalin GRM compound is administered once per day. In embodiments, the heteroaryl-ketone fused azadecalin GRM compound, such as, e.g., relacorilant, is administered with food. Administered "with food" means that the patient has begun eating a meal within 30 minutes, or within one hour, of the time that the heteroaryl-ketone fused azadecalin GRM compound is administered. In alternative embodiments, the heteroaryl-ketone fused azadecalin GRM compound, such as, e.g., relacorilant, is administered to a fasted patient, i.e., to a patient who has not eaten food for at least one hour, or at least two hours, or more hours prior to the administration of the GRM compound. For example, the GRM compound may be administered to a fasted patient in the morning, i.e., to a patient who has not yet eaten the morning meal, and has not eaten since the evening meal of the prior evening.

In embodiments, the GRM administration comprises administration of said GRM at least once per week. In embodiments, the GRM administration comprises administration of said GRM at least twice per week. In embodiments, the GRM administration comprises administration of said GRM at least three times per week. In embodiments, the GRM is administered once per day. In embodiments, the GRM is administered twice per day. In embodiments, the GRM is administered three times per day. In embodiments, the GRM is administered once every other day. In embodiments, the GRM is administered once every third day.

The GRM administration may comprise daily administration of said GRM. In embodiments of daily administration, the GRM is administered once per day. In embodiments, the GRM is administered once per day at about the same time of day each day. In embodiments, the GRM is administered with food. In embodiments, the GRM is administered to a patient without food. In embodiments, the GRM is administered without food in the morning to a patient prior to the patient's morning meal.

In embodiments, the pharmaceutical formulation comprising relacorilant is suitable for administration with another pharmaceutical formulation, e.g., with a pill, tablet, oral solution, injectable, or other formulation including another active ingredient. In all these embodiments, treatment and imaging may be obtained while not leading to significant increases in cortisol, and while not increasing the risk of, or causing, hypokalemia.

II. Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "sample" refers to a biological sample obtained from a human subject. The sample can be any cell, tissue or fluid sample obtained from a human subject. The sample may be, e.g., a blood sample, a saliva sample, a urine sample, or other sample obtained from the patient. Such samples are typically removed from the subject, and, when obtained, become entirely separate from the subject (i.e., are in vitro samples). Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. Thus, in embodiments, samples are in vitro samples and may be analyzed using in vitro methods. The methods disclosed herein are in vitro methods when used with samples obtained from, and removed from, the human subject.

"Patient," "individual" or "subject" is used interchangeably to refer to a human subject. A patient is a human subject suspected of being in need of treatment, or in need of treatment, and may be receiving such needed treatment. In some cases, the individual is suspected of having a tumor, such as a neuroendocrine tumor. A tumor may be an adenoma. A tumor may be a cancerous tumor.

The term "pituitary tumor" as used herein includes, but is not limited to, lactotrophic adenoma or prolactinoma, ACTH-secreting adenoma, somatotrophic adenomas, corticotrophic adenoma, gonadotrophic adenoma, thyrotrophic adenomas, and null cell adenoma. An ACTH-secreting pituitary tumor may be found in the anterior lobe of the pituitary, usually measuring less than about 10 millimeters (mm) in diameter (or, where irregular in shape, less than about 10 mm in their largest linear dimension (the straight line drawn so as to measure the largest extent of the irregular shape)). Most pituitary ACTH-secreting adenomas are small in size (i.e., microadenomas). The present methods are suitable for treating macroadenomas (having a linear dimension greater than 10 mm) and for treating microadenomas (smaller than 10 mm in their largest dimension).

The term "complete resection," in the context of a tumor, refers to surgical removal of a tumor such that the tumor no longer affects ACTH or cortisol levels in the subject. Complete resection can refer to eliminating all of the visible tumor, e.g., pituitary tumor. In some cases, complete resection includes surgical removal of a tumor to provide the subject with a considerable clinical benefit or a curative benefit.

The terms "localize" and "localizing", in the context of a tumor, refer to the determination of the location of the tumor in the body of the patient. For example, a tumor may be localized to the adrenal gland, or the region near the adrenal gland, if an image indicating the presence of the tumor, or label directed to the tumor, is observed on, in, or near to the adrenal gland as indicated by an imaging technique. For example, a tumor may be localized to the pituitary gland, or its stalk, or the region near the pituitary gland, if an image indicating the presence of the tumor, or label directed to the tumor, is observed on, in, or near to the pituitary gland as indicated by an imaging technique.

The terms "identify" and "identifying", in the context of a tumor, refer to determining the presence in a particular tissue or body region, or determining the type, or determining the stage, of a tumor. For example, a tumor found to be in or near the pituitary gland will be identified as a pituitary tumor, while a tumor determined to be in, or near to the adrenal gland (or in any other non-pituitary location) will be identified as an extra-pituitary tumor, and a Cushing's syndrome patient with such a tumor may then be diagnosed as having ectopic Cushing's syndrome. The size, shape (e.g., regular, or irregular with invasion into nearby tissues) of an image may be useful in determining the stage, or invasiveness, of a tumor. Imaging of multiple tumors is useful in determining whether or not the tumor is metastatic; while observing only a single tumor indicates the tumor is not metastatic, or has not yet metastasized.

The term "Cushing's syndrome" refers to a disease caused by prolonged exposure to endogenous or exogenous glucocorticoids. Cushing's syndrome patients often suffer hyperglycemia secondary to hypercortisolism. Symptoms of Cushing's syndrome include, but are not limited to one or more of the following: weight gain, high blood pressure, poor short term memory, poor concentration, irritability, excess hair growth, impaired immunological function, ruddy complexion, extra fat in the neck region, moon face, fatigue, red stretch marks, irregular menstruation, or a combination thereof. Symptoms of Cushing's syndrome can additionally or alternatively include without limitation one or more of the following: insomnia, recurrent infection, thin skin, easy bruising, weak bones, acne, balding, depression, hip or shoulder weakness, swelling of the extremities, diabetes mellitus, elevated white blood cell count, hypokalemic metabolic alkalosis, or a combination thereof.

The term "endogenous Cushing's syndrome" refers to a type of Cushing's syndrome caused by endogenous overproduction of cortisol by a pituitary ACTH-secreting tumor (Cushing's disease), a non-pituitary ACTH-secreting tumor, or a cortisol-secreting tumor (adrenal or extra-adrenal). An ACTH-secreting tumor can be pituitary adenomas, pituitary adenocarcinomas, carincinoid tumors and neuroendocrine tumors Cortisol-secreting tumors include, and are not limited to, cortisol producing adrenal adenomas, adrenocortical carcinomas, primary pigmented micronodular adrenal disease (PPNAD), ACTH independent macronodular adrenal hyperplasia (AIMAH), and extra-adrenal cortisol secreting tumors, e.g., ovarian carcinomas.

The term "exogenous Cushing's syndrome" refers to a type of Cushing's syndrome caused by repeated or prolonged administration of synthetic glucocorticoids, such as prednisone, hydrocortisone, dexamethasone and the like. Subjects receiving long-term steroid replacement therapy, exhibiting symptoms or signs of Cushing's syndrome, and having low serum cortisol levels may have exogenous Cushing's syndrome. A standard reference range for low serum cortisol level is equal to or less than about 4 µg/dL in the morning.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc.

As used herein, the terms "somatostatin" and "SST" refers to the peptide hormone somatostatin and active variants thereof. Somatostatin has at least two naturally occurring active forms: a 14 amino acid form, and a 28 amino acid form. Alternative forms are produced by alternate cleavage of the single preproprotein encoded by this gene. Somatostatin is expressed throughout the body and inhibits the release of numerous secondary hormones by binding to high-affinity G-protein-coupled somatostatin receptors. The fourteen residue form is reported to have the following sequence: Ala-Gly-Cys-Lys-Asn-Phe-Phe-Trp-Lys-Thr-Phe-Thr-Ser-Cys, and to have a disulfide bridge between the two cysteine residues at positions 3 and 14. The twenty-eight residue form is reported to have the following sequence: Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (Disulfide bridge: 17-28). These sequences are reported, for example, by Shen et al., PNAS 79 (150:4575-4579 (1982).

As used herein, the terms "somatostatin analog" and SSA refer to peptide or other molecules active at a somatostatin receptor; as used herein, a somatostatin analog binds to a somatostatin receptor. A somatostatin analog may be a somatostatin receptor agonist (i.e., it may activate a somatostatin receptor), may have partial agonist effects on a somatostatin receptor, may be a partial or may be a strong a somatostatin receptor antagonist, or have other effects when bound to, or in otherwise near to or in contact with a somatostatin receptor. Somatostatin analogs include, without limitation, octreotide, octreotate, pasireotide, lanreotide, pentetreotide, vapreotide, seglitide, cortistatin, and analogs and derivatives thereof. Somatostatin analogs are somatostatin receptor ligands.

As used herein, the term somatostatin receptor refers to a class of G-protein coupled seven transmembrane receptors that bind somatostatin. There are five somatostatin receptor sub-types, referred to as SSTR1-SSTR5 respectively. See, e.g., Trends Pharmacol Sci. 1995 March; 16 (3): 86-8. The full-length human somatostatin receptors include: Type 1, with 391 amino acid residues, NCBI Accession No.: NP_001040.1; Type 2, with 369 amino acid residues, NCBI Accession No.: NP_001041.1; Type 3, with 418 amino acid residues, NCBI Accession No.: NP_001265616.1; Type 4, with 388 amino acid residues, NCBI Accession No.: NP_001043.2; and Type 5, with 364 amino acid residues, NCBI Accession No.: NP_001166031.1.

As used herein, the term "somatostatin receptor ligand," or "somatostatin or somatostatin analog" refers to any ligand of any one of the somatostatin receptor subtypes (SSTR1-SSTR5). In some cases, the ligand is somatostatin. Somatostatin is an inhibitory polypeptide with two primary biologically active forms SST14 and SST28. In some cases, the ligand is a pre- or pre-pro form of somatostatin, or an analog thereof. In some cases, the somatostatin ligand is a somatostatin analog. Somatostatin analogs can be agonists or antagonists of one or more somatostatin receptors. In some cases, the somatostatin ligand preferentially binds or activates somatostatin receptor type 2 (SSTR2). In some cases, the somatostatin receptor ligand preferentially binds or activates somatostatin receptor type 5 (SSTR5). In some cases, the somatostatin receptor ligand preferentially binds or activates SSTR2 and SSTR5. In some cases, the somatostatin receptor ligand preferentially binds or activates SSTR2, SSTR3, and SSTR5. The somatostatin receptor ligand can be administered in a long acting or slow release formulation.

The term "cortisol" refers to the naturally occurring glucocorticoid hormone (also known as hydrocortisone) that is produced by the zona fasciculata of the adrenal gland, and has the structure:

The term "total cortisol" refers to cortisol that is bound to cortisol-binding globulin (CBG or transcortin) and free cortisol (cortisol that is not bound to CBG). The term "free cortisol" refers to cortisol that is not bound to cortisol-binding globulin (CBG or transcortin). As used herein, the term "cortisol" refers to total cortisol, free cortisol, and/or cortisol bound of CBG.

The term "adrenocorticotropic hormone" or "ACTH" refers to a polypeptide-based hormone that is normally produced and secreted by the anterior pituitary gland. ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids. A disruption to the tightly regulated hypothalamus-pituitary-adrenal gland (HPA) axis can cause low levels of ACTH and cortisol, and in turn, secondary adrenal insufficiency.

The term "glucocorticoid" ("GC") refers to compounds that bind to and activate a glucocorticoid receptor. Such a compound may also be referred to as a glucocorticoid receptor agonist, a glucocorticosteroid, a corticoid, a corticosteroid, or a steroid that binds to and activates a glucocorticoid receptor. For example, cortisol, dexamethasone, and prednisone are GCs.

"Glucocorticosteroid" refers to a steroid hormone or steroidal molecule that binds to the glucocorticoid receptor. Glucocorticosteroids are GCs. Glucocorticosteroids are typically characterized by having 21 carbon atoms, an $\alpha,\beta$-unsaturated ketone in ring A, and an $\alpha$-ketol group attached to ring D. They may differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567).

"Glucocorticoid receptor" ("GR") refers to the type II glucocorticoid receptor (GR-II) which specifically binds to cortisol and/or cortisol analogs such as dexamethasone (See, e.g., Turner & Muller, *J Mol Endocrinol*, 2005 35 283-292). The GR is also referred to as the cortisol receptor. The term includes isoforms of GR, recombinant GR and mutated GR. Inhibition constants ($K_i$) against the human GR receptor type II (Genbank: P04150) are between 0.0001 nM to 1,000 nM; preferably between 0.0005 nM to 10 nM, and most preferably between 0.001 nM to 1 nM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. Mifepristone, and such heteroaryl-ketone fused azadecalins compounds as relacorilant (and, e.g., CORT122928, CORT113176) bind to GR and inhibit its activation by cortisol, and so each may be termed a "GRA".

The term "selective inhibitor" in the context of glucocorticoid receptor, refers to a chemical compound that selectively interferes with the binding of a specific glucocorticoid receptor agonist and the glucocorticoid receptor.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33:557-563).

As used herein, the term "mifepristone" refers to 11β-(4-dimethylaminophenyl)-17β-hydroxy-17a-(1-propynyl)-estra-4,9-dien-3-one), also referred to as RU486, or as RU38.486, or as 17-beta-hydroxy-11-beta-(4-dimethyl-aminophenyl)-17-alpha-(1-propynyl)-estra-4,9-dien-3-one). Mifepristone binds to the glucocorticoid receptor (GR), typically with high affinity, and inhibits the biological effects initiated/mediated by the binding of any cortisol or cortisol analog to a GR receptor. Salts, hydrates and prodrugs of mifepristone are all included in the term "mifepristone" as used herein. Thus, used herein, "mifepristone" refers to the molecule that has the following structure:

and to salts, hydrates and prodrugs thereof, and pharmaceutical compositions thereof.

As used herein, the phrase "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic and non-peptidic molecular entities.

Non-steroidal GRA compounds also include glucocorticoid receptor modulators and glucocorticoid receptor antagonists having a heteroaryl-ketone fused azadecalin backbone. Exemplary glucocorticoid receptor modulators and glucocorticoid receptor antagonists having a heteroaryl-ketone fused azadecalin backbone include those described in U.S. Pat. Nos. 8,859,774; 9,273,047; 9,707,223; and 9,956,216, all of which patents are hereby incorporated by reference in their entireties.

Exemplary heteroaryl-ketone fused azadecalin GRM compounds include, without limitation:

(R)-(1-(4-fluorophenyl)-6-((1-methyl-1H-pyrazol-4-yl) sulfonyl)-4,4a,5,6,7,8-hexahydro-1H-pyrazolo[3,4-g] isoquinolin-4a-yl)(4-(trifluoromethyl)pyridin-2-yl) methanone (termed "relacorilant"; also termed "CORT125134"), which has the following structure:

(R)-(1-(4-fluorophenyl)-6-((4-(trifluoromethyl)phenyl) sulfonyl)-4,4a,5,6,-7,8-hexahydro-1H-pyrazolo[3,4-g] isoquinolin-4a-yl)(thiazol-2-yl)methanone (termed "CORT122928"), which has the following structure:

(R)-(1-(4-fluorophenyl)-6-((4-(trifluoromethyl)phenyl) sulfonyl)-4, 4a, 5,6,7,8-hexahydro-1-H-pyrazolo P,4-g] isoquinolin-4a-yl) (pyridin-2-yl)methanone (termed "CORT113176"), which has the following structure:

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

III. Methods of Treatment and Differential Diagnosis

Cushing's syndrome may be diagnosed without knowledge of the source of the excess cortisol or GC action which characterizes the syndrome. Thus, while treatment (e.g., administration of a GRM such as mifepristone or relacorilant) may begin, further diagnostic information may need to be acquired in order to provide the patient with the best treatment for their condition. The present methods provide GRM and GRA treatment, and at the same time utilize that treatment to acquire further information effective to determine whether the patient suffers from a tumor, such as a neuroendocrine tumor. The present methods provide GRM and GRA treatment, and at the same time utilize that treatment to acquire further information effective to treat, to localize, and to identify a tumor in a patient suffering from a tumor, such as a neuroendocrine tumor. The present methods provide GRM and GRA treatment, and at the same time utilize that treatment to acquire further information effective to determine whether a Cushing's syndrome patient suffers from pituitary Cushing's syndrome, or from adrenal Cushing's syndrome, or from exogenous Cushing's syndrome. In some cases, pituitary tumors are not visible on MRI or other imaging technologies, posing significant challenges for surgical resection. In other cases, the tumors are large and may impinge upon surrounding critical structures, thus hampering complete tumor resection. Extensive surgical resection may cause significant damage to normal pituitary tissue leading to hypopituitarism, and in some cases adrenal insufficiency. The methods provided herein can be used to determine whether a patient has a pituitary tumor, an extra-pituitary tumor (e.g., an adrenal tumor), or exogenous Cushing's syndrome. The methods are also useful for postoperative determination of whether a subject has had complete or successful resection of an ACTH secreting tumor.

The methods include obtaining biological samples from a patient suffering from Cushing's syndrome. The sample is typically removed from the patient (i.e., the sample and its analysis are typically utilized in vitro). The biological sample can be saliva, urine, whole blood, plasma, serum, or another biological sample from the patient. In some embodiments, the biological sample is a blood sample. In embodiments, one or both of ACTH and cortisol are measured in plasma from a blood sample obtained from a Cushing's syndrome patient. In embodiments, one or both of ACTH and cortisol are measured in serum from a blood sample obtained from a Cushing's syndrome patient. In some embodiments, the biological sample is saliva. In other embodiments, the biological sample is urine. In embodiments, the sample may be any biological fluid that is not whole blood, plasma or serum.

The present invention provides a method of treating an adrenocorticotropic hormone (ACTH)-secreting tumor in a subject in need thereof. In one aspect, the method comprises administering to the subject a glucocorticoid receptor antagonist GRA and somatostatin, a somatostatin analog (SSA), or a somatostatin receptor ligand, in amounts effective to reduce secretion of ACTH by the tumor. The administering can be simultaneous administration in which the GRA and the somatostatin, SSA or somatostatin receptor ligand are administered in a formulation containing both compounds. Alternatively, the GRA can be administered and then the somatostatin, SSA, or somatostatin receptor ligand can be administered. As yet another alternative, the somatostatin, SSA, or somatostatin receptor ligand can be administered and then the GRA administered.

A. Somatostatin Receptor Ligands

ACTH-secreting tumors can be treated with an effective amount of a GRA, such as a heteroaryl-ketone fused azadecalin GRA (e.g., relacorilant) in combination with a somatostatin receptor ligand such as somatostatin, or a somatostatin analog (SSA). For example, an ACTH-secreting tumor can be treated with effective amounts of a GRA and a somatostatin receptor ligand such as somatostatin, or a somatostatin analog (SSA). In some cases, the somatostatin receptor ligand is a somatostatin receptor agonist.

Exemplary somatostatin receptor ligands include, without limitation, peptide somatostatin receptor ligands, such as those described in U.S. Pat. No. 8,946,154. Exemplary somatostatin receptor ligands further include, without limitation, somatostatin polypeptides from *Oncorhynchus mykiss* and analogs or derivatives thereof, such as those described in U.S. Pat. No. 6,818,739. Exemplary somatostatin receptor ligands further include, without limitation, antibodies that bind to, or bind to and activate one or more somatostatin receptor subtypes (e.g., any one of SSTR1-5, or a combination thereof). Exemplary somatostatin receptor ligands further include, without limitation, non-peptide somatostatin receptor ligands such as those described in U.S. Pat. No. 7,189,856.

Exemplary somatostatin receptor ligands further include, without limitation, the somatostatin receptor ligands described in U.S. Pat. No. 6,358,941. All patents, patent publications, and patent applications discussed herein, both supra and infra, are hereby incorporated by reference in their entireties.

Exemplary somatostatin receptor ligands further include, without limitation, selective somatostatin receptor ligands. For example, the somatostatin receptor ligand can be selective for (e.g., selectively binds to, or selectively activates) one of SSTR1-5. In some cases, the somatostatin receptor ligand is selective for (e.g., selectively binds to, or selectively activates) SSTR1. In some cases, the somatostatin receptor ligand is selective for SSTR2. In some cases, the somatostatin receptor ligand is selective for (e.g., selectively binds to, or selectively activates) SSTR3. In some cases, the somatostatin receptor ligand is selective for (e.g., selectively binds to, or selectively activates) SSTR4. In some cases, the somatostatin receptor ligand is selective for (e.g., selectively binds to, or selectively activates) SSTR5. Somatostatin receptor ligands include somatostatin itself, and somatostatin analogs such as octreotide, lanreotide, pasoreotide, vapreotide, seglitide, cortistatin, pentetreotide, and others.

In some cases, the somatostatin receptor ligand is selective for (e.g., selectively binds to, or selectively activates) two somatostatin receptors selected from the group consisting of SSTR1-5. For example, the somatostatin receptor ligand can be selective for SSTR1 and 4. As another example, the somatostatin receptor ligand can be selective for SSTR2 and 5. In some cases, the somatostatin receptor ligand is selective for (e.g., selectively binds to, or selectively activates) three somatostatin receptors selected from the group consisting of SSTR1-5. In some cases, the somatostatin receptor ligand is selective for (e.g., selectively binds to, or selectively activates) four somatostatin receptors selected from the group consisting of SSTR1-5. Exemplary selective somatostatin receptor ligands include, without limitation, those described in Rohrer et al., 1998, Science 282:737. Exemplary selective somatostatin receptor ligands further include, without limitation, those described in, e.g., U.S. Patent Appl. Pub. No. 20060069017 and U.S. Patent Appl. Pub. No. 20090325863.

In some cases, the somatostatin receptor ligand is selected from the group consisting of octreotide, radiolabeled octreotide, octreotate, pasireotide, lanreotide, pentetreotide, and analogs or derivatives thereof. In some cases, the somatostatin receptor ligand is coupled to a detectable label or a cytotoxic agent. Exemplary detectable labels include spin labels, fluorescent labels, and radionuclides. Exemplary cytotoxic agents include radionuclides and cytotoxic chemotherapeutics. Exemplary somatostatin receptor ligands coupled to a radionuclide include, but are not limited to $^{123}$I-Tyr$^3$-octreotide, $^{111}$In-DTPA-D-Phe$^1$-octreotide, [$^{111}$In-DTPA$^0$]octreotide, [$^{90}$Y-DOTA, Tyr$^3$]octreotide, or [$^{177}$Lu-DOTA, Tyr$^3$]octreotate.

Cortisol Assay

Cortisol levels can be measured in a biological sample, such as saliva, urine, whole blood, serum, plasma, or any other biological fluid taken from a patient suffering from Cushing's syndrome. Such samples are typically analyzed in vitro. In some cases, the same sample is used to measure cortisol level and ACTH level. In other cases, different samples are used to measure cortisol and ACTH levels. For example, cortisol levels can be measured in saliva or urine, and ACTH levels can be measured in plasma. In yet other cases, different samples of the same type are used to measure the levels. Methods for measuring cortisol levels are known to those in the art. Useful assays include immunoassays, e.g., competitive immunoassay, radioimmunoassay, immunofluorometric enzyme assay, and ELISA, competitive protein-binding assay and mass spectrometry, e.g., high-performance liquid chromatography/triple quadrupole-mass spectrometry (LC-MS/MS). Commercial kits for measuring cortisol in sample are available from, e.g., Beckman-Coulter, Seimens, Roche Diagnostics, and the like. Non-limiting examples of an immunoassay include an ADVIA Centaur® Cortisol assay (Siemens Healthcare Global), ARCHITECT i2000SR cortisol (Abbott), Immulite® 2000 Cortisol assay (Siemans Healthcare Global; #L2KCO2), Vitros® ECi Cortisol assay (Ortho Clinical Diagnostics; #107 4053), and Elecsys® Cortisol Immunoassay (Roche Molecular Diagnostics; #11875116160).

Administration of a GRA interferes with, and may reduce or block normal feedback mechanisms which act to limit cortisol production. Clinical experience with mifepristone reveals that mifepristone administration over extended periods of time has resulted in large increases in mean Urinary Free Cortisol (UFC) and in mean serum ACTH. In the absence of effective feedback, as happens, e.g., with long-term mifepristone administration, cortisol levels may rise and lead to hypokalemia, endometrial hypertrophy, vaginal bleeding, or other adverse effects. Such possible adverse effects may be more significant where the patient already suffers from excess cortisol, such as in cases of Cushing's syndrome. In such cases, it is possible that the risk or severity of adverse effects hypokalemia, endometrial hypertrophy, vaginal bleeding, or other adverse effects is more serious than might be the case where the patient did not already suffer from excess cortisol.

Surprisingly, as disclosed herein, and contrary to what had been expected based on experience with, for example, mifepristone, administration of the heteroaryl-ketone fused azadecalin GRM relacorilant does not lead to significant increases in cortisol levels in Cushing's syndrome patients.

Cortisol levels were measured in Cushing's syndrome patients who were administered doses of the heteroaryl-ketone fused azadecalin compound relacorilant. Urinary Free Cortisol (UFC) was measured in these patients over the course of a 12 week study in which ascending doses of relacorilant were administered. Some patients did not continue through to the full 12 weeks of the study. The mean UFC (in units of micrograms cortisol per day (mcg/day) and is shown according to the administered relacorilant dose and time when measured. The upper numbers are the mean values for each group of patients, and the number in parentheses is the standard deviation of the measurements for each group. These results are shown in Table 1.

TABLE 1

| | Group 1: Mean (SD) 24-hr UFC (mcg/day) | | | | | | |
|---|---|---|---|---|---|---|---|
| Relacorilant Dose | Baseline | Wk 2 | Wk 4 | Wk 6 | Wk 8 | Wk 10 | Wk 12 |
| | 215.6 (246.9) | | | | | | |
| 100 mg | | 151.8 (138.3) | 157.0 (113.0) | | | | |
| 150 mg | | | | 145.3 (150.0) | 134.9 (98.1) | | |
| 200 mg | | | | | | 180.9 (180.3) | 211.6 (275.2) |

Cortisol levels were measured in a second group of Cushing's syndrome patients who were administered doses of relacorilant. The doses administered in this study were higher than in the study shown in Table 1. Urinary Free Cortisol (UFC) was measured in these patients over the course of a 16 week study in which ascending doses of relacorilant were administered. Some patients did not continue through to the full 16 weeks of the study. The mean UFC (in units of micrograms cortisol per day (mcg/day) and is shown according to the administered relacorilant dose and time when measured. The upper numbers are the mean values for each group of patients, and the number in parentheses is the standard deviation of the measurements for each group. These results are shown in Table 2.

TABLE 2

Group 2: Mean (SD) 24-hr UFC (mcg/day)

| Relacorilant Dose | Baseline | Wk 2 | Wk 4 | Wk 6 | Wk 8 | Wk 10 | Wk 12 | Wk 14 | Wk 16 |
|---|---|---|---|---|---|---|---|---|---|
| | 228.1 (237.0) | | | | | | | | |
| 250 mg | | 252.1 (223.0) | 218.2 (186.9) | | | | | | |
| 300 mg | | | | 257.4 (196.5) | 149.1 (152.8) | | | | |
| 350 mg | | | | | | 185.4 (170.6) | 249.0 (236.9) | | |
| 400 mg | | | | | | | | 194.1 (166.8) | 203.1 (165.1) |

Cortisol levels obtained for individual patients and the UFC tabular summary (Tables 1 and 2 above) show no significant changes from baseline in UFC. Corresponding mean ACTH levels showed a modest increase from baseline to end of treatment: Group 1, mean ACTH 14.68 pmol/L±10.34 at Week 12 compared with 11.02 pmol/L±8.04 at Baseline: Group 2, mean ACTH 15.56 pmol/L±10.72 at Week 16 or last-observed compared with 12.79 pmol/L±8.36 at Baseline.

As noted above, it is known that cortisol inhibits its own synthesis via negative feedback at the level of the pituitary and the hypothalamus. Mifepristone potently inhibits this negative feedback: administration of mifepristone resulted in a 2.5-fold increase in mean serum ACTH after 16 weeks of treatment and resulted in a 4.6-fold increase in mean UFC (as reported in NDA 202107 Study C1073-400 CSR filed with the US Food and Drug Administration, for Korlym®). Relacorilant, by contrast, is associated with only modest increases in ACTH, and no increases in cortisol concentrations, suggesting it is not a potent antagonist of the negative cortisol feedback, while still being a potent antagonist of GR in peripheral tissues. (The fluctuations in mean UFC levels over time are consistent with the known variability of the test.)

Applicant notes that a lack of drug-induced hypokalemia was observed in Cushing's syndrome patients during a Phase 2 study of relacorilant. The stable cortisol concentrations shown in Table 1 and in Table 2 above likely account for the lack of drug-induced hypokalemia seen in the Phase 2 study.

Applicant notes that such results are in contrast to the results obtained with mifepristone administration. These results demonstrate that mifepristone and relacorilant have different effects on cortisol and ACTH levels in human patients, and that different GRMs can have different effects on ACTH and cortisol. The surprising and different results demonstrated here indicate that the heteroaryl-ketone fused azadecalin GRM relacorilant provide a significant advantages over steroidal GRMs mifepristone and others, for at least the reason that the heteroaryl-ketone fused azadecalin GRM relacorilant does not cause further increases in cortisol levels, and does not cause hypokalemia or other side effects observed with other GRMs.

Administration of a Glucocorticoid Receptor Modulator

Any suitable dose of relacorilant or other heteroaryl-ketone fused azadecalin GRM (e.g., CORT122928 or CORT113176) may be used in combination with somatostatin or a somatostatin analog in the methods disclosed herein. In embodiments, the GRM is administered orally. In some embodiments, the GRM is administered once per day. The dose may be at least about 15 milligrams (mg) per day, and may be about 800 mg/day. In embodiments, the dose may be 25 mg/day, 50 mg/day, 75 mg/day, 100 mg/day, 150 mg/day, 200 mg/day, 250 mg/day, 300 mg/day, 350 mg/day, 400 mg/day, 450 mg/day, 500 mg/day, 550 mg/day, 600 mg/day, 700 mg/day, or 750 mg/day. The dose of relacorilant or other heteroaryl-ketone fused azadecalin GRM may be administered once, or twice, or more times during a day. The dose of relacorilant or other heteroaryl-ketone fused azadecalin GRM may be administered for one day; for two days; for three days; or for more days. In some embodiments, the GRM is administered in at least one dose. In embodiments, the GRM can be administered in 1, 2, 3, 4, 5, 6, 7, 8, 9, 10 or more doses per day. In embodiments, the GRM is administered orally in 1, 2, 3, 4, 5, 6, 7, 8, 9, 10 or more doses per day.

In combination with somatostatin or a somatostatin analog, a patient may be administered at least one dose of heteroaryl-ketone fused azadecalin GRM such as relacorilant in one or more doses over, for example, a 2-48 hour period. In some embodiments, the heteroaryl-ketone fused azadecalin GRM or GRA is administered as a single dose. In other embodiments, the GRM or GRA is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour period, a 36 hour period, a 38 hour period, a 40 hour period, a 42 hour period, a 44 hour period, a 46 hour period or a 48 hour period. In some embodiments, the GRA is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

A biological sample, e.g., plasma, serum, whole blood, urine, or saliva sample can be obtained from the patient at a time or times 2 to 48 hours, e.g., 2, 3, 4, 5, 6, 7, 8, 9, 10, 11, 12, 13, 14, 15, 16, 17, 18, 19, 20, 21, 22, 23, 24, 25, 26,

27, 28, 29, 30, 31, 32, 33, 32, 35, 36, 37, 38, 39, 40, 41, 42, 43, 44, 45, 46, 47 or 48 hours after GRA administration. In some embodiments, the sample is taken from the patient 2 to 24 hours, e.g., 2, 3, 4, 5, 6, 7, 8, 9, 10, 11, 12, 13, 14, 15, 16, 17, 18, 19, 20, 21, 22, 23, or 24 hours after GRA administration.

Exemplary GRMs having a heteroaryl-ketone fused azadecalin backbone, suitable for administration in combination with somatostatin or somatostatin analogs, include those described in U.S. Pat. No. 8,859,774; in U.S. Pat. No. 9,273,047; in U.S. Pat. No. 9,707,223; and in U.S. Pat. No. 9,956,216.

In embodiments, the heteroaryl-ketone fused azadecalin GRM is the compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), also known as "relacorilant" and as "CORT125134", which has the following structure:

In embodiments, the heteroaryl-ketone fused azadecalin GRM is the compound (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone (termed "CORT122928"), which has the following structure:

In embodiments, the heteroaryl-ketone fused azadecalin GRM is the compound (R)-(1-(4-fluorophenyl)-6-((4-(trifluoromethyl)phenyl)sulfonyl)-4, 4a, 5,6,7,8-hexahydro-1-H-pyrazolo P,4-g]isoquinolin-4a-yl) (pyridin-2-yl)methanone (termed "CORT113176"), which has the following structure:

Pharmaceutical Compositions of Glucocorticoid Receptor Antagonists

The compositions administered in the practice of the methods disclosed herein can be prepared in any suitable form, including in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The compositions used in the methods disclosed herein can also be administered by injection, that is, intravenously, intramuscularly, intracutaneously, subcutaneously, intraduodenally, or intraperitoneally. In embodiments, the compositions described herein can be administered by inhalation, for example, intranasally. Additionally, the compositions administered in the practice of the methods disclosed herein can be administered transdermally. The compositions administered in the practice of the methods disclosed herein can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

For preparing pharmaceutical compositions suitable for administration in the practice of the methods disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

Methods of Administration

The compositions administered in the practice of the methods disclosed herein can be delivered by any suitable means, including oral, parenteral (e.g., intravenous injection or intramuscular injection) and topical methods. Transdermal administration methods, by a topical route, can be formulated as applicator sticks, solutions, suspensions, emulsions, gels, creams, ointments, pastes, jellies, paints, powders, and aerosols.

The compositions administered in the practice of the methods disclosed herein may be administered at any time during the day or night. In embodiments of the methods provided herein, a composition is administered in the morning; and may be administered in the morning prior to the morning meal ("fasted" administration) or may be administered in the morning within about 30 minutes or within about one hour after the patient begins eating the morning meal ("fed" administration).

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Compositions administered in the practice of the methods disclosed herein can be administered orally. For example, the compositions administered in the practice of the methods disclosed herein can be administered as a pill, a capsule, or liquid formulation as described herein. Alternatively, compositions can be provided via parenteral administration. For example, the composition can be administered intravenously (e.g., by injection or infusion). Additional methods of administration of the compounds described herein, and pharmaceutical compositions or formulations thereof, are described herein.

In some embodiments, the compositions administered in the practice of the methods disclosed herein are administered in one dose. In other embodiments, the compositions are administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration.

IV. Examples

The following example illustrates, but is not intended to limit, the claimed invention.

Figure 1:
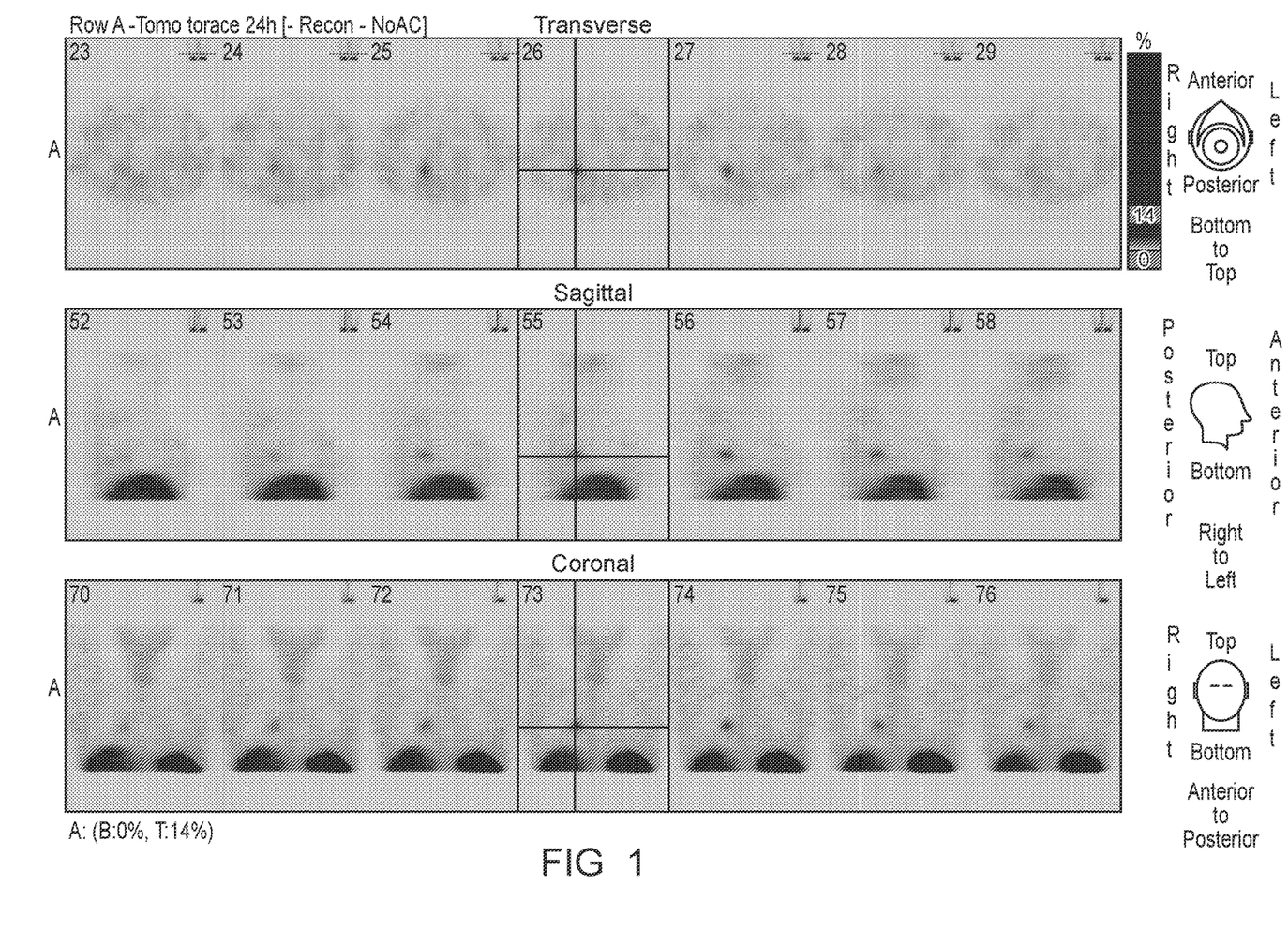
FIG. 1 shows an indium octreoscan image of a Cushing's Syndrome patient having an ectopic tumor, showing faint indications of the ectopic tumor (the dark dot in the right lung/mediastinum shows a mildly octreotide positive lesion). Computer tomography (CT) and magnetic resonance imaging (MRI) images of the patient failed to identify an ectopic tumor in the patient.

Attempts were made to image a tumor hosted by a Cushing's Syndrome patient; however, computer tomography (CT) and magnetic resonance imaging (MRI) images of the patient each failed to provide images by which to identify an ectopic tumor in the patient. In a further attempt to image, and to localize, the tumor in the patient, an indium octreoscan image (patient was administered Octreotide radiolabeled with $^{111}$Indium prior to imaging) was obtained, in which a dot was seen which enabled localization of the tumor to the right lung/mediastinum region of the patient. As shown in FIG. 1, the indium octreoscan image of the Cushing's Syndrome patient shows faint indications of the ectopic tumor (the dark dot in the right lung/mediastinum shows a mildly octreotide positive lesion).

Figure 2:
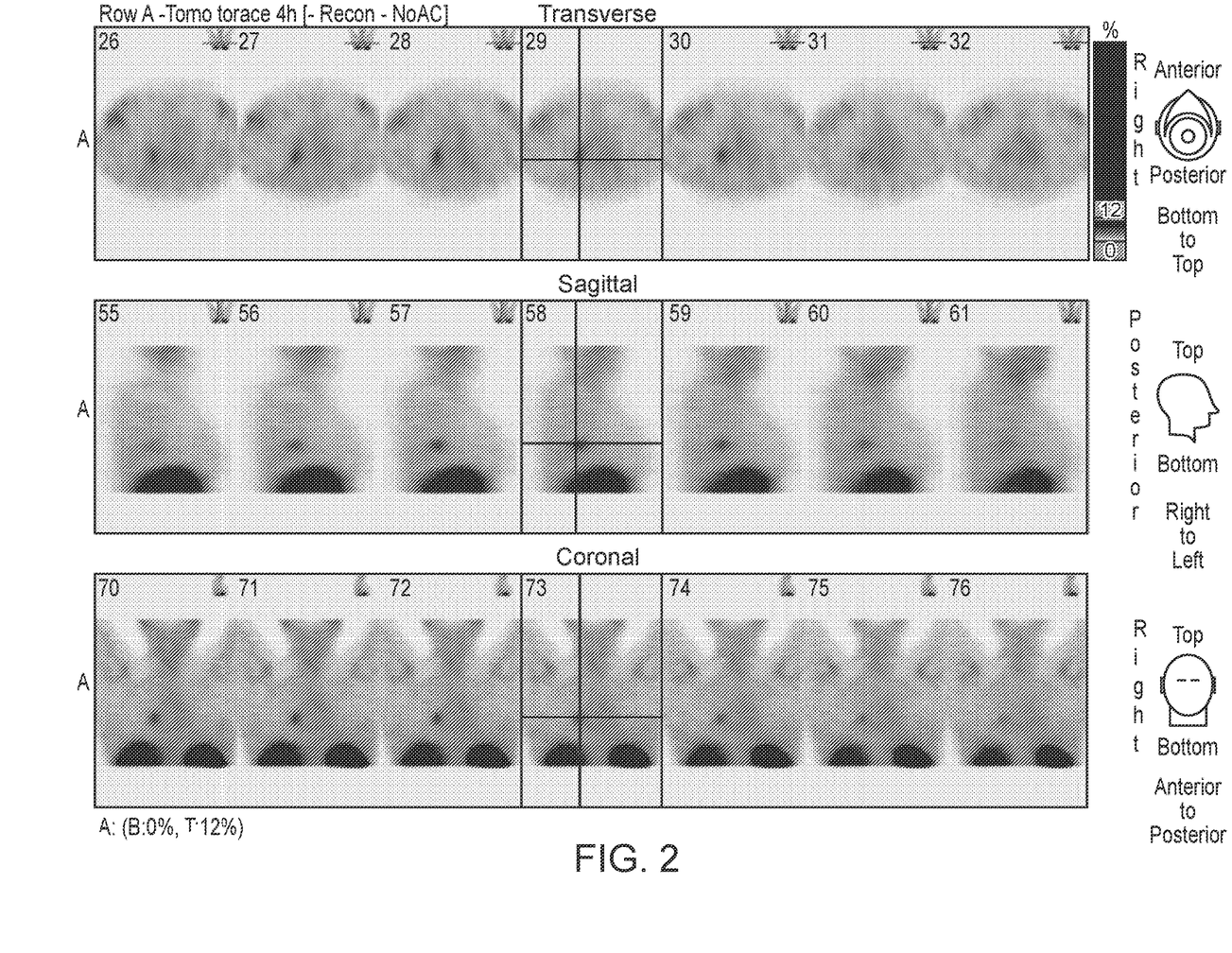
FIG. 2 shows an indium octreoscan image of the same Cushing's Syndrome patient following treatment with relacorilant, a heteroaryl-ketone fused azadecalin glucocorticoid receptor modulator; this image, taken after relacorilant treatment, shows clear images of the ectopic tumor. The relacorilant treatment enhanced the indium octreoscan images of the ectopic tumor.

Relacorilant was then orally administered to the patient once per day for four months. The patient was administered 250 milligrams (mg) per day of relacorilant for four weeks, followed by 300 mg/day relacorilant for the next four weeks, followed by 350 mg/day relacorilant for a further four weeks, and then was administered 400 mg relacorilant for another four weeks. FIG. 2 shows an indium octreoscan image of the same Cushing's Syndrome patient obtained following this four-month treatment with relacorilant. The image of FIG. 2 clearly shows the ectopic tumor. The relacorilant treatment enhanced the indium octreoscan (octreotide radiolabeled with $^{111}$Indium) images of the ectopic tumor.

The indium octreoscan image of FIG. 2 provides a much improved and enhanced image of the tumor in the patient as compared to the image of FIG. 1. It is believed that the improvement in the indium octreoscan image of FIG. 2 as compared to the image shown in FIG. 1 was due to increased somatostatin receptor expression, e.g., due to increased sst2 receptor expression, as compared to that expression prior to the relacorilant treatment.

It will be understood that the exemplary doses of relacorilant can be varied in the methods disclosed herein. For example, in addition to the relacorilant doses of 250 mg/day, 300 mg/day, 350 mg/day, and 400 mg/day, a relacorilant dose of 25 mg/day, or of 50 mg/day, or of 100 mg/day, or of 150 mg/day, or of 200 mg/day, or of 250 mg/day, or of 450 mg/day, or of 500 mg/day, or of 550 mg/day, or other dose of relacorilant may be used in the methods disclosed herein.

It will be further understood that, in addition to the exemplary doses of relacorilant used in the example above, other heteroaryl-ketone fused azadecalin compounds may be administered to the patient in place of, or along with, relacorilant. For example, other heteroaryl-ketone fused azadecalin compounds that may be administered in the practice of methods disclosed herein include CORT122928, CORT113176, and other heteroaryl-ketone fused azadecalin GRM compounds disclosed in U.S. Pat. No. 8,859,774 and continuations thereof.

Although the foregoing invention has been described in some detail by way of illustration and example for purposes of clarity of understanding, one of skill in the art will appreciate that certain changes and modifications may be practiced within the scope of the appended claims. All patents, patent applications, patent publications, and references discussed herein are hereby incorporated by reference in their entireties.

I claim:

1. A method of localizing a neuroendocrine tumor in a patient hosting a neuroendocrine tumor without increasing cortisol levels or risk of hypokalemia in said patient, the tumor having a baseline level of somatostatin receptor expression, the method comprising:
   a) Administering to the patient daily doses of the heteroaryl-ketone fused azadecalin glucocorticoid receptor modulator (GRM) (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (relacorilant) having the structure:

said daily doses of relacorilant comprising daily doses of 250 milligrams per day (mg/day) of relacorilant for four weeks, followed by daily doses of 300 mg/day of relacorilant for four weeks, followed by daily doses of 350 mg/day of relacorilant for four weeks, followed by daily doses of 400 mg/day of relacorilant for four weeks, effective to stimulate the expression of somatostatin receptors (SRs) in said neuroendocrine tumor; then
   b) administering to the patient at least one dose of a radiolabeled somatostatin analog; and then
   c) imaging the patient,
      effective to provide an image of the tumor within the patient,
whereby the neuroendocrine tumor is localized, without leading to significant increases in cortisol, and without increasing the risk of hypokalemia in the patient.

2. The method of claim 1, wherein the method comprises administering a radiolabeled somatostatin analog selected from the group consisting of 123ITyr3-octreotide, 111In-DTPA-D-Phe1-octreotide, [111In-DTPA0]octreotide, [90Y-DOTA, Tyr3]octreotide, 111In-octreotide, 111In-pentetreotide, and [177Lu-DOTA, Tyr3]octreotate.

3. The method of claim 1, wherein said baseline level of somatostatin receptor expression is undetectable with imaging.

4. The method of claim 1, further comprising imaging of labeled somatostatin analogs in the patient effective to localize the tumor within the patient.

5. The method of claim 3, further comprising imaging of labeled somatostatin analogs in the patient following said administration of said heteroaryl-ketone fused azadecalin GRM effective to localize the tumor within the patient.

6. The method of claim 1, wherein said at least one dose of a somatostatin analog administered to the patient is effective to increase the tumor's expression of somatostatin receptors above the baseline amount of somatostatin receptor expression in the tumor.

7. The method of claim 1, wherein said patient suffers from Cushing's syndrome, and said method is effective to treat said Cushing's syndrome.

8. The method of claim 7, wherein said patient suffers from Cushing's Disease, and said method is effective to treat said Cushing's Disease.

* * * * *